US006180757B1

(12) United States Patent
Bogsnes

(10) Patent No.: US 6,180,757 B1
(45) Date of Patent: Jan. 30, 2001

(54) PROCESS FOR THE SEPARATION OF PROTEINS USING A CA++ CONTAINING ELUANT

(75) Inventor: Are Bogsnes, Nivå (DK)

(73) Assignee: Novo Nordisk A/S, Bagsvaerd (DK)

( * ) Notice: Under 35 U.S.C. 154(b), the term of this patent shall be extended for 0 days.

(21) Appl. No.: 09/290,856

(22) Filed: Apr. 13, 1999

(51) Int. Cl.$^7$ ................................................ A61K 38/28
(52) U.S. Cl. .................. 530/305; 530/381; 530/412; 530/416; 530/417
(58) Field of Search .................... 530/412, 417, 530/305

(56) References Cited

U.S. PATENT DOCUMENTS

| 3,649,456 | 3/1972 | Benneville et al. | 195/66 |
| 4,269,605 | * 5/1981 | Dean et al. | 23/230 |
| 5,633,350 | 5/1997 | Fischer et al. | 530/381 |

* cited by examiner

*Primary Examiner*—Christopher S. F. Low
*Assistant Examiner*—Stephan Lu
(74) *Attorney, Agent, or Firm*—Steve T. Zelson, Esq.; Reza Green, Esq.

(57) ABSTRACT

The invention concerns a process of chromatographically separating glycosylated proteins from non-glycosylated proteins by subjecting a solution comprising glycosylated and non-glycosylated proteins to chromatography using a Ca$^{++}$ containing eluant. By using this process a fraction comprising non-glycosylated proteins substantially free from glycosylated proteins is obtained. The process may be applied to the separation of proteins used in the medical industry, such as insulin.

21 Claims, 6 Drawing Sheets

X14:89.98%, mgX14:0.50%, dgX14:0.05%,
desamido:1.32%, X14ethylester:6.60%

X14:98.38%, mgX14:0.02%, dgX14:0.00%, desamido:1.05%

PROCESS FOR THE SEPARATION OF PROTEINS USING A CA++ CONTAINING ELUANT

FIELD OF THE INVENTION

The present invention relates to the process of chromatographically separating glycosylated proteins or protein precursors from non-glycosylated proteins or protein precursors using a $Ca^{++}$ containing eluant.

BACKGROUND AND DESCRIPTION OF THE INVENTION

In the manufacture of proteins or protein precursors the separation of glycosylated proteins from non-glycosylated proteins represents an independent field of research. The industrial implications of the present invention relate to the optimisation of protein purification. It is the purpose of the optimised purification to achieve an end product to be used commercially comprising non-glycosylated proteins, substantially free from glycosylated proteins.

Proteins or protein precursors may originate from yeast expression systems. A correlation between a high expression level and an increase in glycosylated protein precursors has been observed. As a consequence the need for a more efficient process of separating the non-glycosylated proteins from the glycosylated proteins has become even more apparent.

In the yeast expression system a yeast organism produces proteins or protein precursors synthesised intracellularly. The yeast host organism is transformed by an expression vehicle harbouring DNA encoding the desired protein. The process comprises preparing a culture of the transformed yeast host organism, growing the culture and recovering the protein from the culture medium.

Prior art recovery of the desired protein comprised multiple steps of purification using the process of chromatography, such as ion exchange chromatography involving an eluant containing salt. By using the method of reverse phase high performance liquid chromatography (RP-HPLC) the procedure of separating non-glycosylated proteins from glycosylated proteins can be carried out. The eluant used for the elution of the test samples is preferably an organic solvent containing salt, such as KCl. Although various salts have been applied to the organic solvent in the prior art the effect of a $Ca^{++}$ containing eluant has never been disclosed.

In the present context the term eluant is synonymous with the buffer used for elution. The present invention provides an improved purification of the desired protein by using a $Ca^{++}$ containing eluant.

SUMMARY OF THE INVENTION

The present invention provides an improved process of separating glycosylated proteins from non-glycosylated proteins. Accordingly the present invention relates to a process of separating glycosylated proteins from non-glycosylated proteins by subjecting a solution comprising glycosylated and non-glycosylated proteins to RP-HPLC (reverse phase high performance liquid chromatography) using a $Ca^{++}$ containing eluant, and obtaining a fraction comprising non-glycosylated proteins, said fraction substantially free from glycosylated proteins.

In the present invention the term protein refers to all proteins or protein precursors and the term glycosylated proteins includes glycosylated proteins or protein precursors. In a preferred embodiment the protein is insulin or an analogue or precursor thereof.

Another object of the present invention is a fraction obtainable by using the process according to the invention comprising non-glycosylated proteins substantially free from glycosylated proteins.

DRAWINGS

The following is a short description of the figures illustrating the invention. The peaks on the chromatograms are marked on the figures. The term hydrolysis pool indicates the pool used for purification.

DETAILED DESCRIPTION OF THE INVENTION

Figure 1:
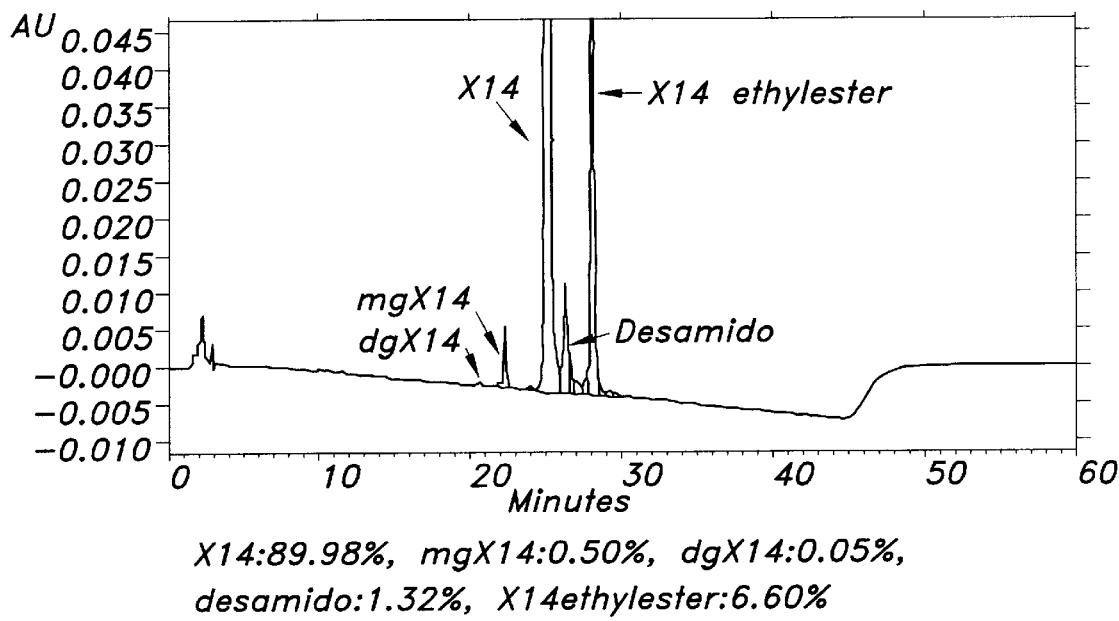
FIG. 1 shows the profile of the hydrolysis pool before the purification using RP-HPLC.

Proteins or protein precursors and analogues thereof may originate from yeast expression systems. In the manufacturing process of proteins or protein precursors the use of chromatographical purification is widespread. The proteins or protein precursors are often subjected to chemical modifications and a series of chromatographical purification steps, such as RP-HPLC, hydrophobe interaction chromatography and ion exchange. The present invention concerns a purification step in which the use of chromatography in the separation of glycosylated proteins from non-glycosylated proteins has proven to be particularly successful. The process comprises subjecting a solution comprising glycosylated and non-glycosylated proteins to chromatography using a $Ca^{++}$ containing eluant, and thereby obtaining a fraction comprising non-glycosylated proteins, said fraction substantially free from glycosylated proteins.

The principle of protein purification using column chromatography is based upon differences in the equilibrium between the stationary and the mobile phase of the proteins to be separated. Using an appropriate combination of stationary and mobile phases, the proteins will leave the column at different intervals.

The chromatography method may be any column chromatography method, preferably RP-HPLC, or hydrophobe interaction chromatography.

In the present invention the advantage is the increased purity of the fraction of non-glycosylated proteins. The fraction of glycosylated proteins may consist of mono-glycosylated proteins and poly-glycosylated proteins. The present invention provides means for the improvement of the separation of glycosylated proteins, such as mono-glycosylated proteins and poly-glycosylated proteins, from non-glycosylated proteins.

Another aspect of the present invention is obtaining an additional fraction comprising glycosylated proteins and substantially no non-glycosylated proteins.

Depending on the composition of the starting material the glycosylated proteins may be mono-glycosylated, or at least a part of the glycosylated proteins may be di-glycosylated, or at least a part of the glycosylated proteins may be poly-glycosylated.

Compared to other chromatography methods, where a $Ca^{++}$ containing eluant is not used, the present invention holds the advantage of a higher productivity due to an increased column load of approximately 50%. The efficiency of the purification is influenced by the ligand and by the particle pore size of the matrix. The particle pore size may vary dependent upon the nature of the protein to be purified. When the protein is insulin or an analogue thereof the optimal column matrix is 200 Å and the column may be loaded up to 150–250 mg/cm² when the starting material is of the given composition described below, and the length of the column used is as described below.

The column temperature may be 10–30° C., preferably 18–25° C. Any temperature, lower than the preferred temperature range may lead to an increase in expenses of purification by slowing the process down.

By using methods for the purification of non-glycosylated proteins described by prior art, it has not yet been possible to achieve a fraction substantially free from glycosylated proteins while maintaining such a high productivity. However the introduction of the present invention has improved the purification process markedly, and the final fraction comprising non-glycosylated proteins is substantially free from glycosylated proteins.

By using the means of the present invention a fraction comprising non-glycosylated proteins is obtainable, wherein said fraction is substantially free from glycosylated proteins, whilst the productivity level of said fraction is increased.

The present invention has proved to be especially advantageous in the separation of glycosylated insulins from non-glycosylated insulins. Preferably, the concentration of glycosylated insulins in the fraction of non-glycosylated insulin is less than 0.2%, such as less than 0.1%. This is approximately a ten-fold reduction in the concentration of glycosylated insulins compared to the starting material.

The starting material for the separation or purification may be any protein solution comprising non-glycosylated and glycosylated proteins. The starting material may be the medium obtained from yeast expression systems directly, or the starting material may have been subjected to several purification or chemical modification steps prior to the separation according to the invention.

Without being bound by theory it is the general belief that the interaction of the proteins with $Ca^{++}$ leads to a change of the proteins hydrophobicity. It is the differential change in hydrophobicity effected by minor molecular differences, such as sugar or ester groups, that is believed to constitute the very core of the principle behind the separation of glycosylated proteins from non-glycosylated proteins or otherwise modified proteins. The degree to which the proteins change in hydrophobicity upon the presence of $Ca^{++}$ are dependent on the nature of the protein, such as the presence of glycosyl and/or ester groups.

Thus, the method according to the present invention may be used to separate any variants of proteins, wherein the hydrophobicity of the variants are changed differently by the addition of $Ca^{++}$ in the eluant.

The application of $Ca^{++}$ to an organic solvent-based eluant greatly enhances separation of glycosylated proteins from non-glycosylated proteins compared to that of an eluant comprising $K^+$ or $Na^+$ or $NH_4^+$ alone or in combination. This fact is due to the selective effect of $Ca^{++}$ on the increase in hydrophobicity of non-glycosylated proteins. In addition to $Ca^{++}$ ions the eluant may comprise cations such as $K^+$ and/or $Na^+$ and/or $NH_4^+$ ions. The $Ca^{++}$ ions may be supplied by any suitable source, such as $CaCl_2$.

The present inventor has found that the combination of $Ca^{++}$ and $K^+$ ions in the eluant improves the chomatographic properties. In the present invention the preferred composition of the eluant is a mixture of KCl and $CaCl_2$ where the $Ca^{++}$ concentration in the eluant is below 300 mM, such as below 200 mM, preferably below approximately 100 mM, more preferably approximately 5–50 mM, and a $K^+$ concentration of 100–300 mM, such as approximately 200 mM. Within the given concentration ranges the concentration of KCl in the eluant preferably exceeds the eluants $CaCl_2$ concentration.

When $Na^+$ and/or $NH_4^+$ ions are present the $Na^+$ and/or $NH_4^+$ concentration in the eluant is 100–300 mM, such as approximately 200 mM.

The preferred pH value of the eluant is higher than the isoelectric point for the protein, and the analogues thereof, to be separated. With respect to insulin, most insulins have an isoelectric point not below pH 5.0.

In the present invention the retention volume is between 5 and 10 CV (column volume) in an isocratic eluation.

The eluant may in principle comprise any organic solvent. The organic solvent may be ethanol, methanol, isopropanol or acetonitril. In the present invention the preferred organic solvent is ethanol having a concentration in the range of 20–30% by weight.

The invention further relates to a fraction obtainable by using the process according to the invention comprising non-glycosylated proteins, wherein the fraction is substantially free from glycosylated proteins. The invention is advantageously used for separating insulins, wherein the fraction may have a concentration of glycosylated insulins of less than 0.2% by weight/volume.

The purified non-glycosylated proteins, in particular insulins, may find application in any technical field, such as the medical field, such as the treatment of diabetes.

Experimentals

The following is a description of the experiments performed to improve the separation of non-glycosylated insulins from glycosylated insulins. By using an eluant containing $Ca^{++}$ ions it was found that the separation is greatly enhanced, and a more pure end product of non-glycosylated insulins were achieved.

Materials and methods

General methods

All experiments were performed on pools containing glycosylated and non-glycosylated forms of the insulin analogue X14 or the insulin analogue DesB30. X14 has the same a and b chains as do human insulin, the only diffence being the substitution in position b28 of proline in human insulin for aspartic acid in X14. DesB30 has the same a and b chains as do human insulin, the only diffence being the lack of threonine in position b30.

All percentages are given as % by weight.

Examples 1–3 were conducted with X14, and example 4 was conducted with DesB30.

Analysis

Selected pools were fractionated and analysed on RP-HPLC. The pools were analysed for the main product as well as for glycosylated variants. Fractions of X14 were also analysed for ethylester.

Chromatography

The chromatography was done on a BioCAD HPLC system from PerSeptive Biosystems equipped with a 6 or 3 mm flow cell. The following data were constant for all experiments, except when specified as a variable in an experiment:

| | |
|---|---|
| Matrix | FD* 200Å C18 15 μm reverse phase particles |
| Temperature | 25° C. |
| Column | 250 mm × I.D. 10 mm (0.785 cm$^2$), column volume = 19.6 ml |
| Flow | 2.5 cm/min |
| Regeneration buffer | 70% ethanol + 1M acetic acid |

*FD: Fuji Davison

Buffer composition
General experimental conditions

All chemicals used for buffers were of analytical grade. Water was of WFI (water for injection) quality. All buffers were adjusted to pH 7.0 with HCl.

| Process parameters: Column operation | | |
|---|---|---|
| Equilibration | 16% ethanol | 5 CV* |
| Application | | variable |
| Wash | 16% ethanol | 1 CV |
| Elution | | <12 CV |
| Regeneration | | 5 CV |

*(CV = column volume)

EXAMPLE 1
Purification with buffer systems containing CaCl$_2$

| Test parameters: Eluant | Eluation [EtOH] | Load (mg/cm$^2$) | Fig No. |
|---|---|---|---|
| 2.5 g/kg Tris, 100 mM CaCl$_2$ | 28% | 30 | 3 |
| 2.5 g/kg Tris, 50 mM CaCl$_2$ | Approx. 29% | 30 | 4 |

Results and discussion

Figure 3:
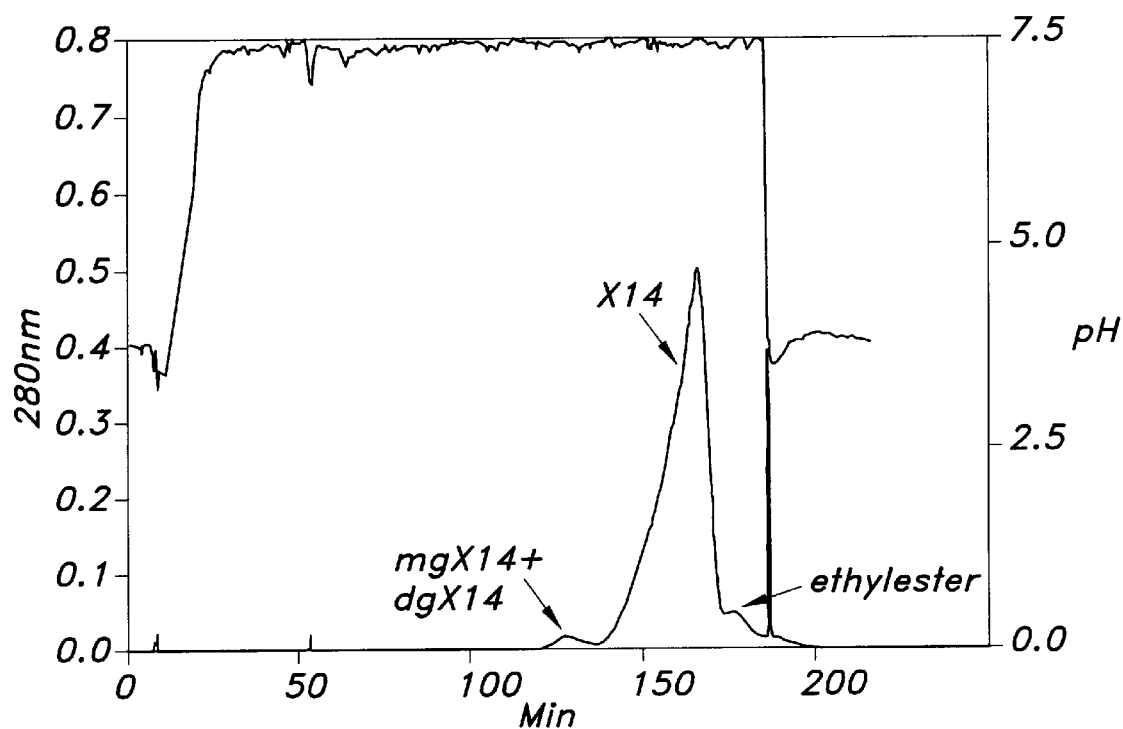
FIG. 3 shows the separation profile of the RP-HPLC run using a buffer system with 100 mM $CaCl_2$. The peak representing the glycosylated X14 forms is almost baseline separated.
Figure 4:
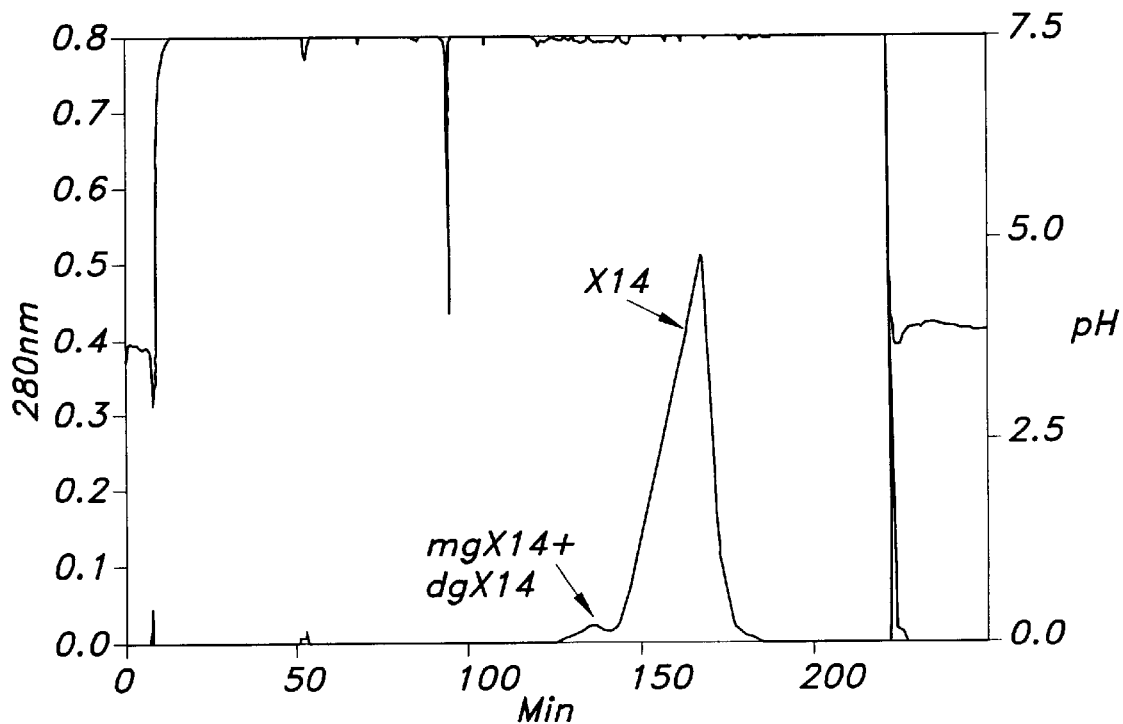
FIG. 4 shows the separation profile of the RP-HPLC run using a buffer system with 50 mM $CaCl_2$.

CaCl$_2$ was dramatically different from any other salt tested (for comparison see Example 2). With 100 mM (FIG. 3), the peak representing the glycosylated X14 forms was almost baseline separated. The X14 peak was broad and had a very low preflank slope, but the postflank was on the other hand very steep. In the run with 50 mM (FIG. 4) the ethanol concentration during the run was manually adjusted, and therefore cannot be directly compared, but nevertheless, it indicates a very similar result.

It was noteworthy that the hydrophobicity of X14 was selectively increased by CaCl$_2$, demonstrated by the higher ethanol concentration necessary for elution of X14 compared to KCl alone (see Example 2 for comparison). Glycosylated X14 forms and ethylester seemed to be less affected by CaCl$_2$.

Thus, the experiments show that CaCl$_2$ buffers selectively increase the X14 hydrophobicity, resulting in a complete separation of the glycosylated X14 forms.

EXAMPLE 2 (COMPARISON)
Purification with buffer systems containing KCl

These tests were conducted to show the purification profile of the processes using KCl without CaCl$_2$.

| Test parameters: Eluant | Eluation [EtOH] | Load (mg/cm$^2$) | Fig No. |
|---|---|---|---|
| 10 mM Bis-tris, 50 mM KCl | 26.6% | 30 | 5 |
| 10 mM Bis-tris, 200 mM KCl | 26.6% | 30 | 6 |

Results and discussion

Figure 5:
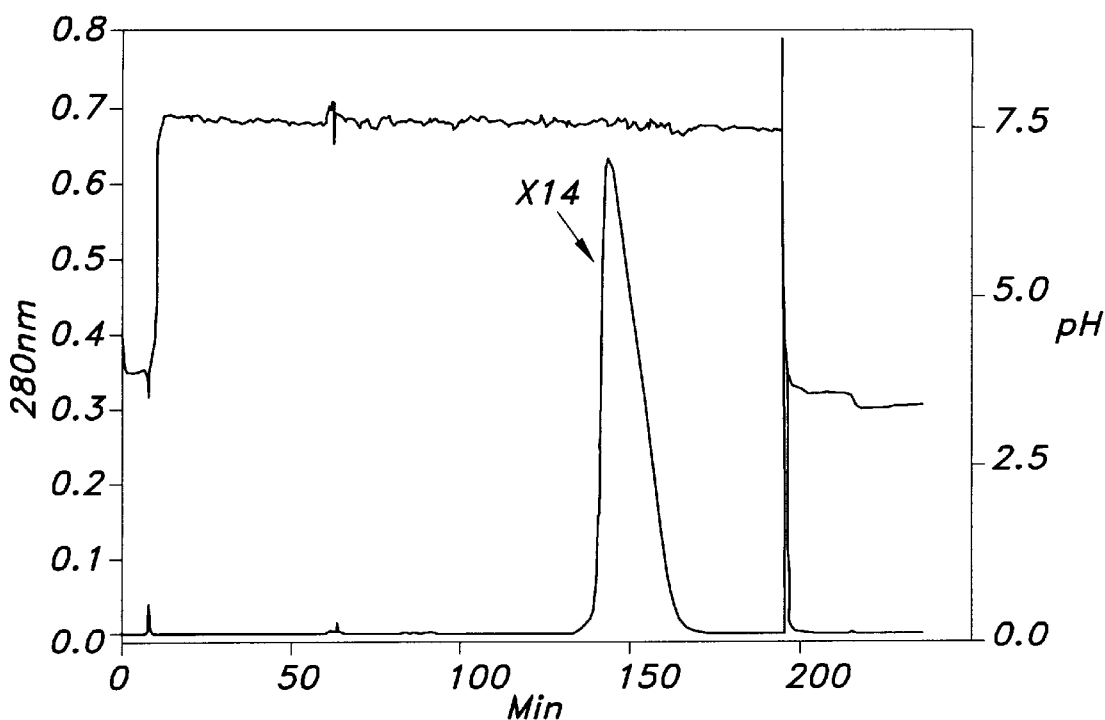
FIG. 5 shows the separation profile of the RP-HPLC run using a buffer system with 50 mM KCl.
Figure 6:
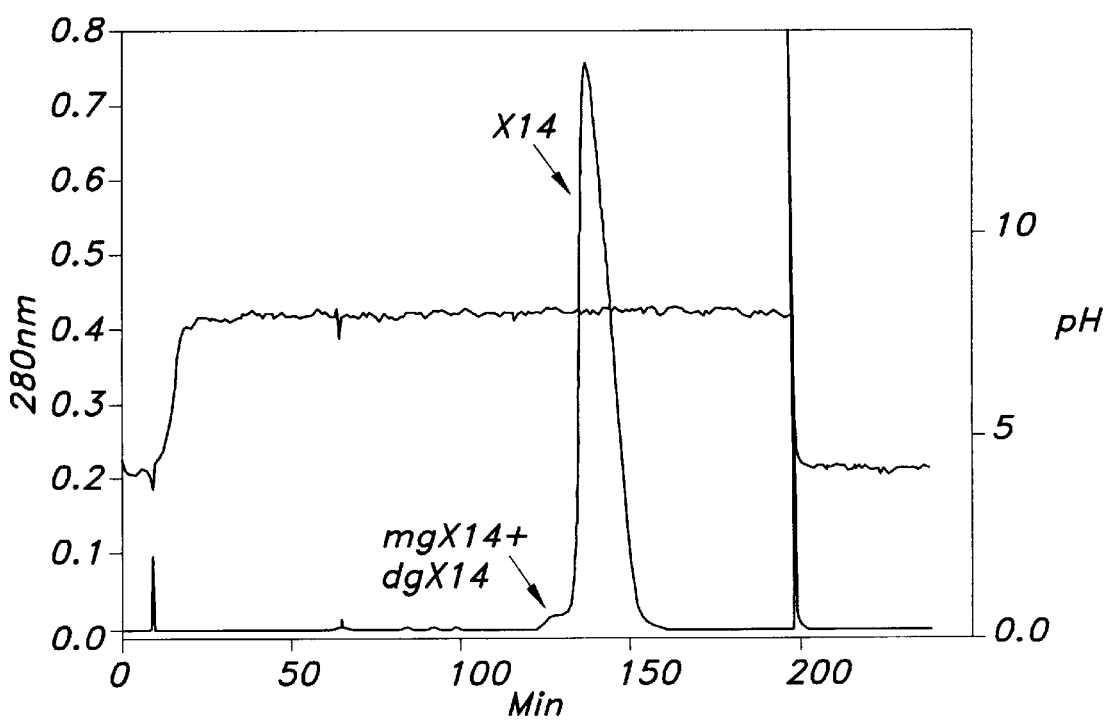
FIG. 6 shows the separation profile of the RP-HPLC run using a buffer system with 200 mM KCl.

With a KCl concentration of 50 mM (FIG. 5), the preflank of the eluting peak started with a steep slope followed by a more steep slope. This indicates the presence of smaller, closely eluting peaks. Increasing the KCl concentration to 200 mM (FIG. 6) improved the separation but not to the level of separation using a Ca$^{++}$ containing eluant. These observations were confirmed by analysis of the fractions.

EXAMPLE 3
Purification with buffer systems containing KCl and CaCl, combined

These tests were performed to examine the influence of a buffer system combining KCl and CaCl$_2$ on the simultaneous separation of ethylester and glycosylated X14 forms.

Test 1

| Test parameters: Eluant | Eluation [EtOH] | Load (mg/cm$^2$) | Fig No. |
|---|---|---|---|
| 2.5 g/kg Tris, 25 mM CaCl$_2$, 100 mM kCl | 28% | 30 | 7 |
| 2:5 g/kg Tris, 12.5 mM CaCl$_2$, 150 mM KCl | 28% | 30 | 8 |

Results and discussion 1

Figure 7:
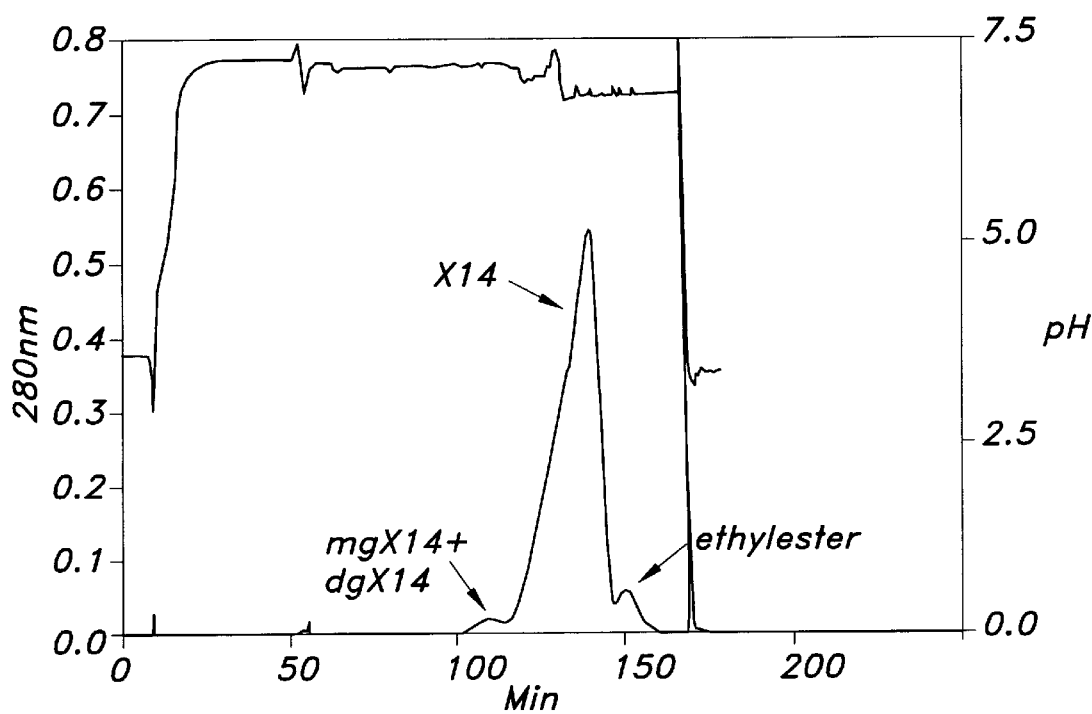
FIG. 7 shows the separation profile of the RP-HPLC run using a buffer system with 100 mM KCl and 25 mM $CaCl_2$.
Figure 8:
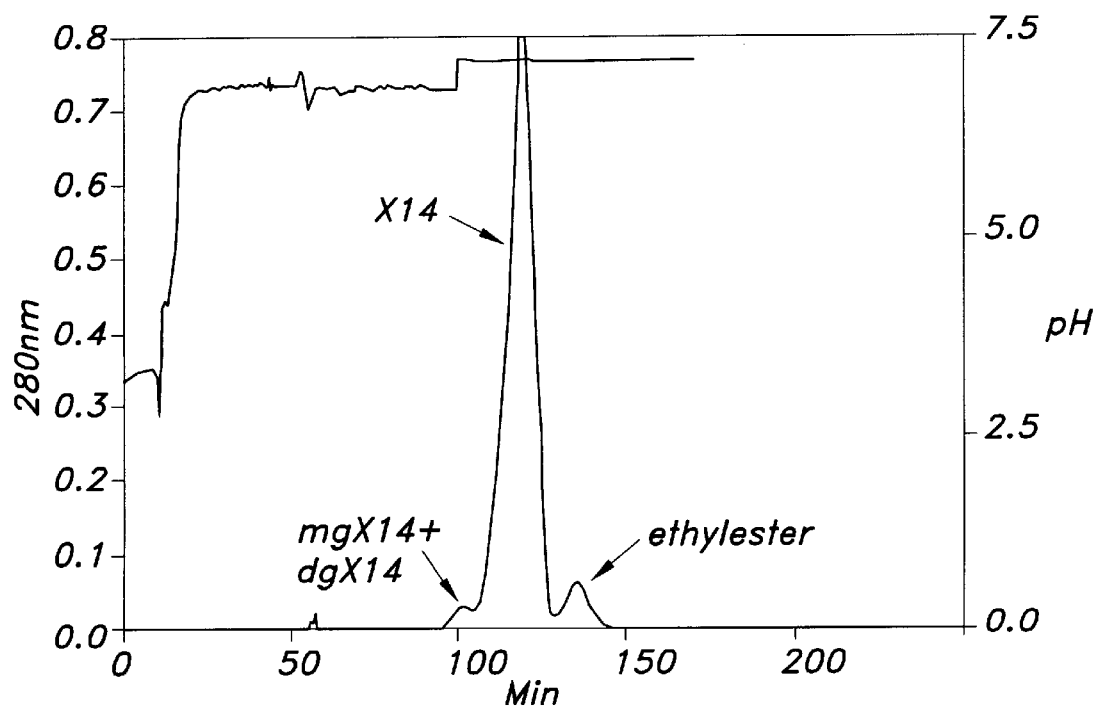
FIG. 8 shows the separation profile of the RP-HPLC run using a buffer system with 150 mM KCl and 12.5 mM $CaCl_2$.

A mixture of KCl and CaCl$_2$ (100/25 mM) resulted in a better separation of the ethylester than with CaCl$_2$ buffers alone (FIG. 7). The combination 150/12.5 mM gave an even better separation of the ethylester (FIG. 8). However, at the same time the peak representing the glycosylated X14 forms was less separated, but still much better than with KCl alone. The slow rise of the preflank slope was less pronounced.

The experiments show that both KCl and CaCl$_2$ are important buffer components. The experiments show that the presence of Ca$^{++}$ in the buffer greatly improves the purification process. Increasing Ca$^{2+}$ concentrations selectively increased the hydrophobicity of X14 when compared to the ethylester and the glycosylated X14 forms.

Test 2

This experiment was conducted as in test 1 except for the following changed parameters: 180 mM KCL and 5 mM CaCl$_2$, ethanol 27.4% (eluation) and the load was 150 mg/cm$^2$. The profile of the pool was examined before and after purification.

Results and discussion 2

Figure 2:
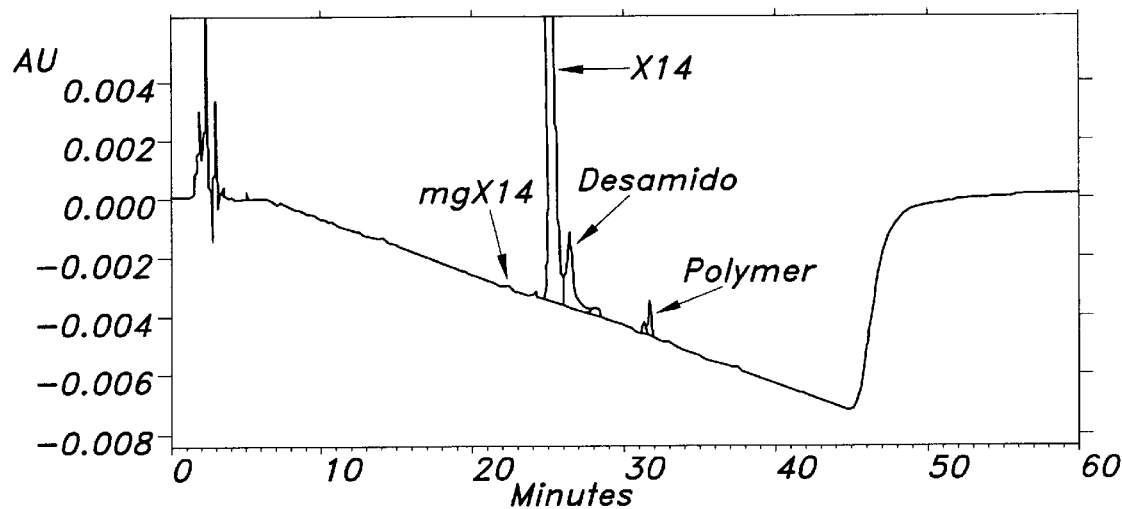
FIG. 2 shows the profile of the hydrolysis pool after purification using RP-HPLC.

By this purification it is possible to obtain a fraction of non-glycosylated X14 substantially free from glycosylated X14. FIG. 1 shows the profile of the pool before purification. As indicated the content of X14 in the pool was 89.98%. FIG. 2 shows the profile of the pool after purification. Here it is demonstrated that the content of X14 increased to 98.38% after the purification, and the content of mono-glycosylated X14 decreased significantly from 0.50% to 0.02%.

EXAMPLE 4

Purification of DesB30 using buffer systems with or without $CaCl_2$

These tests were performed to demonstrate the effect of $Ca^{++}$ on the elution profile of the insulin analogue DesB30. All experiments were performed at pH: 7.2. The following data were used:

| | |
|---|---|
| Matrix | FD* 200Å C18 15 µm reverse phase particles |
| Temperature | 22° C. |
| Column | 250 mm × I.D. 10 mm (0.785 cm²), column volume = 19.6 ml |
| Flow | 3.0 cm/min |
| Regeneration buffer | equilibrated with 16% ethanol, 0.1M citric acid |

*FD: Fuji Davison

| Process parameters: Column operation | | |
|---|---|---|
| Equilibration | 16% ethanol | 2.5 CV* |
| Application | | variable |
| Wash | 16% ethanol | 1 CV |
| Elution | | <12 CV |
| Regeneration | | 2 CV |

*(CV = column volume)

Test 1

| Test parameters: Eluant | Eluation [EtOH] | Load (mg/cm²) | Fig No. |
|---|---|---|---|
| 15 mM Tris, 5 mM maleic acid, 0 mM $CaCl_2$, 200 mM KCl | 27% | 190 | 9 |
| 15 mM Tris, 5 mM maleic acid, 20 mM $CaCl_2$, 200 mM KCl | 27% | 190 | 9 |

Figure 9:
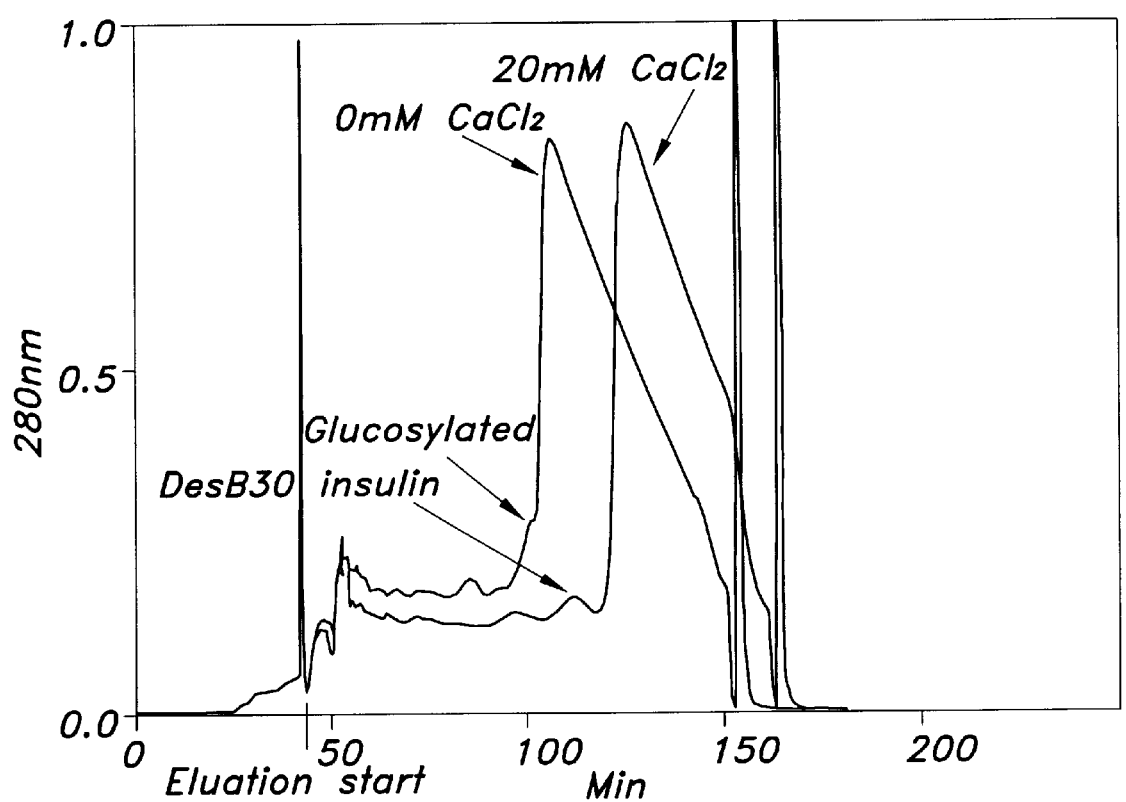
FIG. 9 shows the separation profile of a RP-HPLC run for the purification of the insulin analogue DesB30 using one buffer system without $CaCl_2$ and another buffer system with 20 mM $CaCl_2$.

FIG. 9 shows the difference between the elution profile of DesB30 when using an eluant containing 20 mM $CaCl_2$ compared to using an eluant containing no $CaCl_2$. It is clear that when $Ca^{++}$ is present in the eluant the separation of non-glycosylated insulin from glycosylated insulin is improved.

| Test parameters: Eluant | Eluation [EtOH] | Load (mg/cm²) | Fig No. |
|---|---|---|---|
| 15 mM Tris, 5 mM maleic acid, 0 mM $CaCl_2$, 200 mM KCl | 26.8% | 190 | 10 |
| 15 mM Tris, 5 mM maleic acid, 20 mM $CaCl_2$, 200 mM KCl | 27.8% | 190 | 10 |

Compared to test 1 the ethanol concentration (elution) was changed to obtain similar retention.

Figure 10:
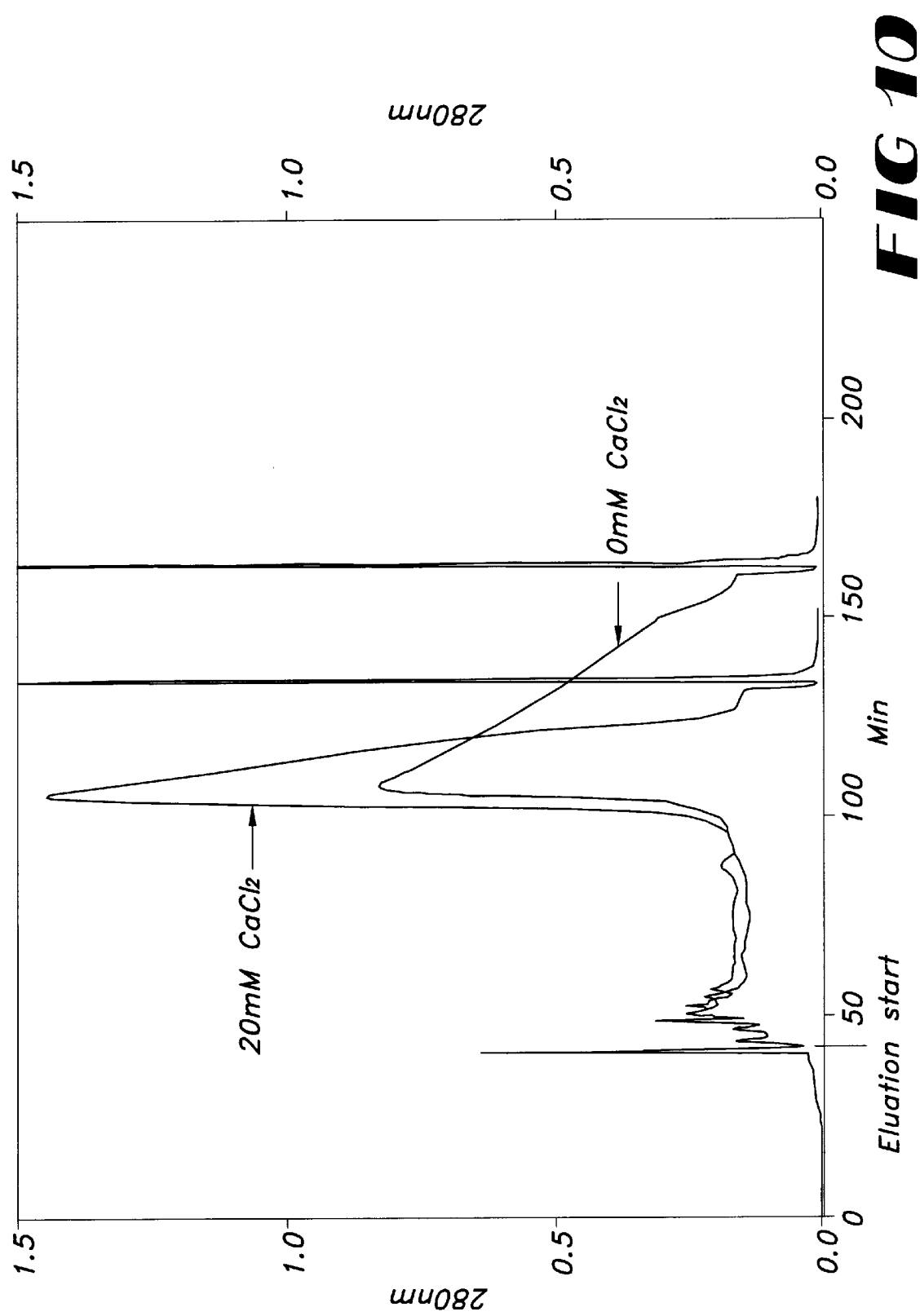
FIG. 10 shows the separation profile of an analytical RP-HPLC run for the purification of the insulin analogue DesB30 using one buffer system without $CaCl_2$ and another buffer system with 20 mM $CaCl_2$.

FIG. 10 shows the difference between the elution profile of DesB30 when using an eluant containing 20 mM $CaCl_2$ compared to the profile when using an eluant containing no $CaCl_2$.

The pool content was examined before and after elution.

Before the elution there was 1.22% mono-glycosylated DesB30 in the elution pool. After purification using a $Ca^{++}$ containing eluant the amount of mono-glycosylated DesB30 had been reduced approximately fivefold to 0.21%. When compared to the 1.10% of mono glycosylated DesB30 left after the elution using an eluant containing no $Ca^{++}$, it is clear that when $Ca^{++}$ is present in the eluant the separation of non-glycosylated insulin from glycosylated insulin is improved.

What is claimed is:

1. A process of separating glycosylated insulins from non-glycosylated insulins, said method comprising (i) subjecting a solution comprising glycosylated and non-glycosylated insulins to reverse-phase high performance liquid chromatography (RP-HPLC) us a $Ca^{++}$-containing eluant, wherein said eluant contains $Ca^{++}$ at a concentration effective to enhance the separability of said glycosylated and non-glycosylated insulins in said RP-HPLC; and (ii) obtaining a fraction comprising non-glycosylated insulins, said fraction being substantially free from glycosylated insulins.

2. A process according to claim 1, further comprising (iii) obtaining a fraction comprising glycosylated insulins, said additional fraction being substantially free from non-glycosylated insulins.

3. A process according to claim 1, wherein the glycosylated insulins are mono-glycosylated.

4. A process according to claim 1, wherein at least a part of the glycosylated insulins are poly-glycosylated.

5. A process according to claim 1, wherein the eluant further comprises additional cations selected from the group consisting of $NH_4^+$, $K^+$, and $Na^+$.

6. A process according to claim 1, wherein the eluant comprises $CaCl_2$ or Ca-acetate.

7. A process according to claim 1, wherein the $Ca^{++}$ concentration in the eluant is below 300 mM.

8. A process according to claim 5, wherein the $NH_4^+$ concentration in the eluant is 100–300 mM.

9. A process according to claim 5, wherein the $K^+$ concentration in the eluant is 100–300 mM.

10. A process according to claim 5, wherein the $Na^+$ concentration in the eluant is 100–300 mM.

11. A process according to claim 1, wherein the eluant has a pH value above the isoelectric point for the insulins.

12. A process according to claim 1, wherein the temperature is 10–30° C.

13. A process according to claim 7, wherein the eluant further comprises an organic solvent selected from the group consisting of ethanol, methanol, isopropanol, and acetonitrile.

14. A process according to claim 13, wherein the eluant has an ethanol concentration of 20–30% w/w.

15. A process according to claim 1, wherein the $Ca^{++}$ concentration in the eluant is below 200 mM.

16. A process according to claim 1, wherein the $Ca^{++}$ concentration in the eluant is below 100 mM.

17. A process according to claim 1, wherein the $Ca^{++}$ concentration in the eluant is below 50 mM.

18. A process according to claim 1, wherein the $NH_4^+$ concentration in the eluant is approximately 200 mM.

19. A process according to claim 1, wherein the $K^+$ concentration in the eluant is approximately 200 mM.

20. A process according to claim 1, wherein the $Na^+$ concentration in the eluant is approximately 200 mM.

21. A process according to claim 1, wherein the temperature is 18–25° C.

* * * * *

UNITED STATES PATENT AND TRADEMARK OFFICE
CERTIFICATE OF CORRECTION

PATENT NO. : 6,180,757 B1
DATED : January 30, 2001
INVENTOR(S) : Are Bogsnes

Page 1 of 1

It is certified that error appears in the above-identified patent and that said Letters Patent is hereby corrected as shown below:

Title page,
Please add -- (30) Foreign Application Priority Data: DK 0528/98, filed April 15, 1998 --.

Column 7,
Line 57, please add -- Test 2 --.

Column 8,
Line 18, please delete "us", and insert -- using --.

Signed and Sealed this

Twenty-seventh Day of November, 2001

Attest:

NICHOLAS P. GODICI
*Attesting Officer*  *Acting Director of the United States Patent and Trademark Office*